United States Patent [19]

Baasner et al.

[11] Patent Number: 4,888,430
[45] Date of Patent: Dec. 19, 1989

[54] FLOURINE-CONTAINING 5-TRIHALOGENOMETHYL-ISOXAZOLES AND A PROCESS FOR THEIR PREPARATION

[75] Inventors: Bernd Baasner, Leverkusen; Alexander Klausener, Stolberg; Pieter Ooms, Krefeld, all of Fed. Rep. of Germany

[73] Assignee: Bayer Aktiengesellschaft, Leverkusen, Fed. Rep. of Germany

[21] Appl. No.: 125,296

[22] Filed: Nov. 25, 1987

[30] Foreign Application Priority Data

Dec. 12, 1986 [DE] Fed. Rep. of Germany ....... 3642453

[51] Int. Cl.$^4$ ........................................... C07D 261/08
[52] U.S. Cl. .................................... 548/247; 548/378
[58] Field of Search ........................................ 548/247

[56] References Cited

U.S. PATENT DOCUMENTS 4,000,150 12/1976 Cambon et al. .................. 548/247
4,742,060 5/1988 Shiokawa et al. ................ 514/252

FOREIGN PATENT DOCUMENTS 0091022 10/1983 European Pat. Off. .
2847766 5/1979 Fed. Rep. of Germany .
2801579 7/1979 Fed. Rep. of Germany .
3212137 10/1983 Fed. Rep. of Germany ...... 548/247
68187 11/1986 Israel .

OTHER PUBLICATIONS

Derwent Abstract for DE3212137 (10/6/83), Number 83-783792/41.
Quilico et al., in *Five-and Six–Membered Compounds with Nitrogen and Oxygen* (Interxcience Publ.) pp. 43, 49, 50 (1962).
*Advanced Organic Chemistry* by Jerry March, p. 342 (1977).
Del'tsova et al., Chemical Abstracts, vol. 75, No. 63669d (1971).
Galluci et al., Chemical Abstracts, vol. 89, Number 215273 (1978).
*Ullmann's Encyclopedia of Industrial Chemistry* (5th Ed.), p. 354 (1988).

*Primary Examiner*—Mukund J. Shah
*Assistant Examiner*—E. Bernhardt
*Attorney, Agent, or Firm*—Sprung Horn Kramer & Woods

[57] ABSTRACT

The present invention relates to new 5-trihalogenomethyl-isoxazoles of the formula (I)

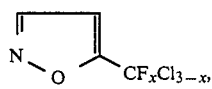

(I)

in which x represents 1, 2 or 3, and a process for their preparation by reacting the corresponding trichloromethylisoxazole with a fluorinating agent.

2 Claims, No Drawings

FLUORINE-CONTAINING 5-TRIHALOGENOMETHYL-ISOXAZOLES AND A PROCESS FOR THEIR PREPARATION

The present invention relates to new 5-trihalogenomethyl-isoxazoles of the formula (I)

  (I)

in which x represents 1, 2 or 3.

The formula (I) embraces the following individual compounds: 5-trifluoromethyl-isoxazole, 5-difluorochloro-methyl-isoxazole and 5-fluorodichloromethyl-isoxazole.

The present invention furthermore relates to a process for the preparation of 5-trihalogenomethyl-isoxazoles of the formula (I)

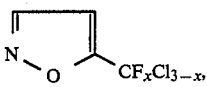  (I)

in which x represents 1, 2 or 3, characterized in that 5-trichloromethyl-isoxazole is reacted with a fluorinating agent. Examples of suitable fluorinating agents are hydrogen fluoride and antimony trifluoride. Anhydrous hydrogen fluoride is preferably used.

It is extremely surprising that the new 5-trihalogenomethyl-isoxazoles of the formula (I) are obtainable by reacting 5-trichloromethyl-isoxazole with fluorinating agents, such as hydrogen fluoride and/or the Lewis acid antimony trifluoride, if appropriate in the presence of further Lewis acids (for example antimony chlorides). In fact, reactions of the isoxazole ring system with hydrogen fluoride and/or antimony trifluoride (for example addition reactions) analogous to other reactions of isoxazoles with acids (see, for example, A. Quilico, Isoxazole and Related Compounds, pages 5–94, in The Chemistry of Heterocyclic Compounds (Ed. A. Weisberger), Volume 17, New York-London, 1982) were to be expected on the one hand and, on the other hand, also elimination of the CCl$_3$ radical from the isoxazole ring under the fluorination conditions used.

The 5-trichloromethyl-isoxazole required as a starting material for the process according to the invention, and its preparation, are known (see DE-OS No. (German Published Specification) 3,212,137). The preparation of 5-difluorochloromethyl- and 5-trifluoromethyl-isoxazole can be carried out according to the invention using not only 5-trichloromethyl-isoxazole as a starting material but also 5-fluorodichloromethyl-isoxazole or mixtures of this with 5-trichloromethyl-isoxazole. For the preparation, according to the invention, of 5-trifluoromethyl-isoxazole, it is also possible to use 5-difluorochloromethyl-isoxazole or mixtures of this with 5-fluorodichloromethyl-isoxazole and/or 5-trichlbromethyl-isoxazole as a starting material. 5-Fluorodichloromethyl- and 5-difluorochloromethyl-isoxazole and mixtures containing these may be intermediate stages which are passed through in the preparation, according to the invention, of relatively highly fluorinated products (=5-difluorochloromethyl- or 5-trifluoromethyl-isoxazole).

Where hydrogen fluoride is used as a fluorinating agent, it is preferably employed in a large stoichiometric excess, since the excess can then serve as a solvent. For example, 3 to 1,500 mol of hydrogen fluoride, in particular anhydrous hydrogen fluoride, can be employed per mol of starting material (=5-trichloromethyl- and/or 5-fluorodichloromethyl- and/or 5-difluorochloromethyl-isoxazole). Where antimony trifluoride is used as a fluorinating agent, it is possible, for example, to use the stoichiometric amount or an excess of up to 30 mol %, and, in the case of the preparation of 5-trifluoromethyl-isoxazole, even an excess of up to 200 mol %. Other fluorinating agents can be used, for example, in corresponding amounts to antimony trifluoride.

The fluorination according to the invention can be carried out, if appropriate, in the presence of customary fluorination catalysts, as described, for example, in Houben-Weyl, Methoden der Organischen Chemie, Georg-Thieme-Verlag, Stuttgart, Vol. 5/3, page 124 et seq. (1962). Antimony pentachloride, mixtures and/or reaction products of antimony trichloride and/or antimony trifluoride with chlorine and/or hydrogen fluoride are particularly suitable. Such reaction products can, for example, correspond to the formula (II)

  (II)

in which n represents an integer or fractional number from 1 to 5.

Antimony pentachloride is preferably used. If fluorination catalysts are employed, they can be used, for example, in amounts of 0.005 to 1 mol per mol of starting compound.

The fluorination according to the invention is carried out in general at elevated temperature. For example, the reaction can be carried out at 50° to 250° C. The pressure can be chosen, for example, in the range from 1 to 50 bar. Where hydrogen fluoride is used as the fluorinating agent, the process is preferably carried out batchwise in a closed vessel under the autogenous pressure generated at the particular reaction temperature, or an inert gas, for example nitrogen, is additionally forced up to a total pressure of up to 80 bar. If antimony trifluoride is used as the fluorinating agent, the reaction is preferably carried out under atmospheric pressure or pressures of to 5 bar.

When hydrogen fluoride is used as the fluorinating agent, suitable reaction times are, for example, those in the range from 1 to 24 hours.

The process according to the invention can also be carried out continuously, the fluorination being effected, for example, with anhydrous hydrogen fluoride in an appropriate reactor in the gas phase. In this procedure, both reactants (for example the 5-trichloromethyl-isoxazole and the hydrogen fluoride) can be present in the gas phase and pressures of up to 50 bar can be employed.

The presence of a solvent (with the exception of excess hydrogen fluoride) is generally not necessary.

In the preparation of 5-fluorodichloromethyl-, 5-difluorochloromethyl- or 5-trifluoromethyl-isoxazole, slightly different reaction conditions in each case are preferred. In general, the following reaction conditions promote the formation of relatively highly fluorinated products (see formula (I), x=2 or 3):
  relatively large excess amounts of fluorinating agent, in particular where antimony trifluoride is used,
  presence of fluorination catalysts, in particular in relatively large amounts, relatively high reaction temperatures,
relatively high reaction pressures, in particular where hydrogen fluoride is used as the fluorinating agent, and
relatively long reaction times.

For the preparation of 5-difluorochloromethyl- and 5-trifluoromethyl-isoxazole, however, it is not necessary to choose all these reaction conditions close to the upper limit of the ranges stated further above. In this case, it is generally sufficient to choose one or two of these reaction conditions close to the upper limit of the ranges stated further above and to choose the other reaction conditions as desired, or to choose all reaction conditions in about the middle or in the upper half of the ranges stated further above.

The preparation, according to the invention, of 5-fluorodichloromethyl-isoxazole (formula (I), $x=1$) is preferably carried out using 3 to 500 mol, particularly preferably using 5 to 50 mol, of hydrogen fluoride per mol of starting compound or using an excess of 5 to 20 mol % of antimony trifluoride, in the absence of a fluorination catalyst, at temperatures in the range from 50° to 150° C., particularly preferably 80° to 130° C., under pressures of 1 to 30 bar, particularly preferably 1 to 15 bar, and using reaction times of 2 to 10, particularly preferably 2 to 5, hours.

The preparation, according to the invention, of 5-difluorochloro-isoxazole (formula (I), $x=2$) is preferably carried out using 3 to 1,000 mol, particularly preferably 8 to 80 mol, of hydrogen fluoride per mol of starting compound or using an excess of 10 to 30 mol % of antimony trifluoride, with the addition of 0.005 to 0.2 mol of fluorination catalyst, at temperatures of 50° to 200° C., particularly preferably 80° to 160° C., under pressures of 2 to 50 bar, particularly preferably 10 to 20 bar (where hydrogen fluoride is used as the fluorinating agent) or under pressures of 1 to 5 bar, particularly preferably under atmospheric pressure (where antimony trifluoride is used as the fluorinating agent) and using reaction times of 2 to 15, particularly preferably 3 to 8, hours.

The preparation, according to the invention, of 5-trifluoromethyl-isoxazole (formula (I), $x=3$) is preferably carried out using 10 to 1,500 mol, particularly preferably 15 to 200 mol, of hydrogen fluoride per mol of starting compound or using an excess of 50 to 200 mol % of antimony trifluoride, with the addition of 0.005 to 1 mol of fluorination catalyst, at temperatures from 80° to 250° C., particularly preferably from 100° to 190° C., under pressures of 15 to 80 bar, particularly preferably 20 to 35 bar, when hydrogen fluoride is used as the fluorinating agent, and under pressures of 1 to 5 bar, particularly preferably under atmospheric pressure, when antimony trifluoride is used as the fluorinating agent, and using reaction times of 2 to 20, particularly preferably 5 to 10, hours.

When antimony trifluoride is used as the fluorinating agent, it is also possible to choose reaction times which are shorter than those stated above and are, for example, between 0.1 and 10, particularly preferably between 0.5 and 5, hours in all preparation processes.

The preferred and particularly preferred reaction conditions described above for the preparation of 5-difluorochloromethyl-isoxazole and 5-trifluoromethyl-isoxazole are independent of whether 5-trichloromethyl-isoxazole or a corresponding, already partially fluorinated product is used as the starting material.

The process according to the invention can be carried out, for example, in such a way that 5-trichloromethyl-isoxazole and the particular fluorinating agent, if appropriate together with a fluorination catalyst, are combined at room temperature or with cooling (the latter particularly where hydrogen fluoride is used as the fluorinating agent), if appropriate an initial pressure is generated with nitrogen, the mixture is then heated to the reaction temperature and cooled again when the reaction is complete, the resulting hydrogen chloride is let down when closed reaction vessels are used, and the reaction mixture is worked up. This working up can be carried out, for example, by first removing excess fluorinating agent and any fluorination catalyst present, for example by distillation and/or washing with water, and then subjecting the crude product thus obtained to fractionation under atmospheric or reduced pressure. However, the reaction mixture can also be worked up by a different method, for example by adding water (if necessary only after the hydrogen fluoride has been distilled off), separating off the organic phase, washing the aqueous phase with an inert organic solvent and subjecting the combined organic phases to fractionation under atmospheric or reduced pressure.

The new 5-trihalogenomethyl-isoxazoles of the formula (I)

in which x represents 1, 2 or 3, are valuable intermediate products from which, for example, plant protection agents, pharmaceuticals and dyestuffs can be prepared.

The examples which follow illustrate the present invention without limiting its scope.

EXAMPLES

EXAMPLE 1

(Synthesis of 5-fluorodichloromethyl-isoxazole from 5-trichloromethyl-isoxazole)

93.25 g (0.5 mol) of 5-trichloromethyl-isoxazole were added dropwise at 0° to +3° C. in the course of 60 minutes to 120 ml of anhydrous hydrogen fluoride, which had been initially taken in a stirred steel autoclave. After nitrogen had been forced in until the pressure reached 5 bar, the mixture was heated to 115° C., the pressure reaching 12 bar, and was left at this temperature for 3.5 hours. After cooling, the mixture was let down, the excess hydrogen fluoride was distilled off from the reaction vessel under 150 mbar and the crude product was then distilled off from the reaction vessel under 20 mbar. The crude product thus obtained was washed with twice 200 ml of water, and the organic phase was dried with magnesium sulphate and distilled under 20 mbar. 57 g (=67% of theory) of 5-fluorodichloromethyl-isoxazole (formula (I), $x=1$) having a boiling point of 52° to 54° C. under 20 mbar and a refractive index $nD^{20}$ of 1.4550 were obtained.

EXAMPLE 2

(Synthesis of 5-difluorochloromethyl-isoxazole from 5-trichloromethyl-isoxazole 93.25 g (0.5 mol) of 5-trichloromethyl-isoxazole were added dropwise at −5° to 0° C. in the course of 40 minutes to 180 ml of anhydrous hydrogen fluoride and 0.5 ml of antimony pentachloride, which had been initially taken in a stirred steel autoclave. After nitrogen was forced in until the pressure reached 18 bar, the mixture was heated to 150° C. and left to react at this temperature for 4 hours. After cooling, the excess hydrogen fluoride was distilled off under 150 mbar and the crude product washed with three times 200 ml of water. After being dried with magnesium sulphate, the organic phase was distilled under atmospheric pressure. 43.2 g (=56.5% of theory) of 5-difluorochloromethyl-isoxazole (formula (I), x=2) having a boiling point of 92° to 93° C. and a refractive index of 1.4033 were obtained.

EXAMPLE 3

(Synthesis of 5-trifluoromethyl-isoxazole from 5-trichloromethyl-isoxazole)

56 g (0.3 mol) of 5-trichloromethyl-isoxazole, 80 g of antimony trifluoride and 1 ml of antimony pentachloride were combined at room temperature, then heated to an internal temperature of 140° C. and left to react at this temperature for 90 minutes under reflux. Thereafter, the volatile constituents were distilled off under atmospheric pressure (top temperature 70° to 120° C.) and the crude product obtained was redistilled over a 10 cm packed column. 26.8 g (=65.2% of theory) of 5-trifluoromethyl-isoxazole (formula (I), x=3) having a boiling point of 79° to 80° C. under atmospheric pressure and a refractive index of 1.3493 were obtained.

At 81° to 110° C., 16 g of a further fraction were obtained which, according to analysis by gas chromatography, consisted of 68.8% by weight of 5-difluorochloromethyl-isoxazole and 30.3% by weight of 5-trifluoromethyl-isoxazole. This fraction was re-used in subsequent, analogous batches, together with 5-trichloromethyl-isoxazole.

EXAMPLE 4

(Synthesis of 5-trifluoromethyl-isoxazole from 5-fluorodichloromethyl-isoxazole)

70 g (0.1 mol) of 5-fluorodichloromethyl-isoxazole were added dropwise at $-5°$ to 0° C. in the course of 20 minutes to 60 ml of anhydrous hydrogen fluoride and 0.5 ml of antimony pentachloride, which were initially taken in a stirred steel autoclave. After nitrogen had been forced in until the pressure reached 25 bar, the mixture was heated to 180° C. and left to react at this temperature for 8 hours. After cooling, the excess hydrogen fluoride was distilled off under 150 mbar and the crude product was washed with twice 50 ml of water. After being dried with magnesium sulphate, the organic phase was distilled under atmospheric pressure. 5.7 g (=42% of theory) of 5-trifluoromethyl-isoxazole (formula (I), x=3) having a boiling point of 78° to 80° C. and a refractive index of 1.3498 were obtained.

EXAMPLE 5

(Synthesis of 5-trifluoromethyl-isoxazole from 5-difluorochloromethyl-isoxazole)

30.7 g (0.2 mol) of 5-difluorochloromethyl-isoxazole, 70 g of antimony trifluoride and 1 ml of antimony pentachloride were combined at room temperature, then heated to a temperature of about 140° C. (bath temperature) and left to react for 90 minutes under reflux. Thereafter, the volatile constituents were distilled off under atmospheric pressure (top temperature 65° to 105° C.) and the crude product obtained was redistilled over a 10 cm packed column. 19.75 g (=72.1% of theory) of 5-trifluoromethylisoxazole (formula (I), x=3) having a boiling point of 79° to 80° C. under atmospheric pressure and a refractive index $nD^{20}$ of 1.3495 were obtained.

EXAMPLE 6

(Characterization of the products prepared according to Examples 1 to 3)

The $^1$H NMR spectrum, the $^{19}$F NMR spectrum and the mass spectrum of each of the products prepared according to Examples 1 to 3 were recorded.

CDCl$_3$ (=deuterochloroform) served as the solvent in all NMR measurements. TMS (=tetramethylsilane) was used as an internal standard for the $^1$H NMR measurements, and CF$_3$COOH (=trifluoroacetic acid) as an external standard for the $^{19}$F NMR measurements.

The NMR measurements were carried out with a Bruker WP 80 FT spectrometer with a $^1$H/$^{19}$F dual sample holder, at a measurement frequency of 80 MHz (for $^1$H) and 75.39 MHz (for $^{19}$F).

The mass spectrographic data were determined with a mass spectrometer of the type Finnigan MAT 112 (EI mode, 70 eV).

In the table below, the NMR data and the main peaks of the mass spectra are listed.

TABLE 1

| Compound | $^1$H NMR δ[ppm] | $^{19}$F NMR | mass spectrum |
|---|---|---|---|
| 3  4<br>⟨N−O⟩−CFCl$_2$<br>from Example 1 | 8,35 (4-H)<br>6,68 (3-H) | −27,47 m/e | 169/171 (M$^+$)<br>134/136 (M$^+$−Cl),<br>base-peak |
| 3  4<br>⟨N−O⟩−CF$_2$Cl<br>from Example 2 | 8,32 (4-H)<br>6,68 (3-H) | −27,40 m/e | 153/155 (M$^+$)<br>134/136 (M$^+$−F)<br>118 (M$^+$−Cl),<br>base peak |
| 3  4<br>⟨N−O⟩−CF$_3$<br>from Example 3 | 8,38 (4-H)<br>6,76 (3-H) | −14,39 m/e | 137 (M$^+$),<br>base peak<br>118 (M$^+$−F) |

All $^1$H and $^{19}$F NMR signals appear as slightly split singlets, and the signals of the proton bonded at position 3 in each case are additionally split by long-range coupling with fluorine. Analogously, all fluorine resonance signals exhibit fine structure.

EXAMPLE 7

Conversion of 5-trifluoromethylisoxazole to an insecticide, and its action 0.92 g (0.04 mol) of sodium were dissolved in 25 ml of ethanol, 5.48 g (0.04 mol) of 5-trifluoromethylisoxazole were added at 0° C. and the mixture was stirred for 15 minutes at room temperature. 16.16 g (0.04 mol) of N-(2,6-dichloro-4-trifluoromethylphenyl)-trifluoroacethydrazide bromide were added dropwise to this mixture, while cooling, and stirring was continued for a further 10 hours at 25° C. After the precipitated sodium bromide had been filtered off, the filtrate was evaporated down and separated by column chromatography.

1.65 g (9.3% of theory) of 4-cyano-3,5-di-(trifluoromethyl)-1-(2,6-dichloro-4-trifluoromethyl-phenyl)pyrazole of melting point 88°–92° C. were obtained (referred to below as active compound). LD$_{100}$ test 2 parts by weight of active compound were taken up in 1,000 parts by volume of acetone. 2.5 ml of the active compound solution were pipetted into a Petri dish. A filter paper having a diameter of about 9.5 cm was present on the bottom of the Petri dish. The Petri dish was left standing open until the solvent had completely evaporated. Thereafter, 20 animals of the species Blattella germanica were introduced into the Petri dish and covered with a glass lid.

The condition of the test animals was checked 3 days after the experiments had been set up. This test showed that the active compound had a superior action compared with the prior art.

LT$_{100}$ test for Diptera 2 parts by weight of active compound were taken up in 1,000 parts by volume of acetone. 2.5 ml of the active compound solution were pipetted into a Petri dish. A filter paper having a diameter of about 9.5 cm was present on the bottom of the Petri dish. The Petri dish was left standing open until the solvent had completely evaporated. Thereafter, 20 animals of the species *Musca domestica* (resistant) were introduced into the Petri dish and covered with a glass lid.

The condition of the test animals was checked continuously. The time required for a 100% knock-down effect was determined. This test showed that the active compound had a superior action compared with the prior art.

What we claim is:

1. A 5-trihalogenomethyl-isoxazole of the formula

in which x represents 1,2, or 3.

2. A 5-trihalogenomethyl-isoxazole according to claim 1, wherein the 5-trihalogenomethyl-isoxazole is selected from the group consisting of 5-trifluoromethyl-isoxazole, 5-difluorochloromethyl-isoxaxole and 5-fluorodichloromethyl-isoxazole.

* * * * *